(12) United States Patent
Hand et al.

(10) Patent No.: US 8,580,348 B2
(45) Date of Patent: Nov. 12, 2013

(54) TREATMENT OF TEXTILE MATERIALS

(75) Inventors: Geoffrey Hand, Halesowen (GB); Robert Hicklin, Ashby de la Zouch (GB)

(73) Assignee: Rhodia Operations, Aubervilliers (FR)

( * ) Notice: Subject to any disclaimer, the term of this patent is extended or adjusted under 35 U.S.C. 154(b) by 157 days.

(21) Appl. No.: 13/132,561

(22) PCT Filed: Nov. 2, 2009

(86) PCT No.: PCT/EP2009/064419
§ 371 (c)(1),
(2), (4) Date: Jul. 15, 2011

(87) PCT Pub. No.: WO2010/063524
PCT Pub. Date: Jun. 10, 2010

(65) Prior Publication Data
US 2011/0262647 A1    Oct. 27, 2011

(30) Foreign Application Priority Data

Dec. 3, 2008  (GB) .................................. 0822029.5

(51) Int. Cl.
*B05D 3/10* (2006.01)
(52) U.S. Cl.
USPC .......... 427/342; 427/337; 427/340; 427/341; 427/352; 427/353; 427/354
(58) Field of Classification Search
None
See application file for complete search history.

(56) References Cited

U.S. PATENT DOCUMENTS

| | | | | |
|---|---|---|---|---|
| 3,899,619 A | * | 8/1975 | Daigle et al. | 427/396 |
| 3,922,406 A | * | 11/1975 | Chapin | 427/402 |
| 3,933,122 A | * | 1/1976 | Wagner | 118/718 |
| 4,068,026 A | * | 1/1978 | Wagner | 427/341 |
| 4,084,027 A | * | 4/1978 | Berni et al. | 427/393.3 |
| 4,137,346 A | * | 1/1979 | Wagner | 427/341 |
| 4,145,463 A | | 3/1979 | Cole | |
| 4,244,692 A | * | 1/1981 | Claiborne | 8/127.1 |
| 5,135,541 A | * | 8/1992 | Cole et al. | 8/127.1 |
| 5,378,243 A | * | 1/1995 | Lei et al. | 8/196 |
| 5,688,429 A | * | 11/1997 | Zakikhani et al. | 252/8.61 |
| 5,942,006 A | | 8/1999 | Cole | |
| 2010/0304030 A1 | * | 12/2010 | Dermeik et al. | 427/337 |

FOREIGN PATENT DOCUMENTS

| | | |
|---|---|---|
| EP | 0294234 | 7/1988 |
| EP | 0470640 | 2/1992 |
| GB | 2294479 | 5/1968 |
| GB | 1439608 | 6/1976 |
| GB | 1439609 | 6/1976 |
| GB | 2205868 | 12/1988 |
| GB | 2252570 | 8/1992 |
| GB | 2290562 | 1/1996 |

OTHER PUBLICATIONS

International Search Report; International Application No. PCT/EP2009/064419; filed Nov. 2, 2009.

* cited by examiner

*Primary Examiner* — Erma Cameron
(74) *Attorney, Agent, or Firm* — Hunton & Williams LLP

(57) ABSTRACT

The present invention provides a method for treating textile material to confer flame retardant properties, the method comprising the steps of impregnating the material with an aqueous solution of a treatment agent which is a poly(hydroxyorgano)phosphonium compound; drying the impregnated material; curing the dried impregnated material with ammonia to produce a cured, water-insoluble polymer which is mechanically fixed within the fibers of the material; oxidizing the cured polymer to convert trivalent phosphorus to pentavalent phosphorus; and washing and drying the material; wherein one or both of steps (d) and (e) result in the co-production of an aqueous effluent; and wherein the conditions are controlled such that the atomic ratio of N:P present on the material increases during step (c) by 0.8 or more.

14 Claims, No Drawings

TREATMENT OF TEXTILE MATERIALS

CROSS-REFERENCE TO RELATED APPLICATIONS

This application is the U.S. National Phase of International Application No. PCT/EP2009/064419 filed on Nov. 2, 2009, which claims priority to Great Britain Application No. GB 0822029.5 filed Dec. 3, 2008, both of which are incorporated by reference herein in their entireties.

FIELD OF THE INVENTION

The present invention relates to a method of treating textile materials to confer flame-retardant properties, which method is adapted so as to also control the composition of the effluent produced during the method.

BACKGROUND

A known process for the flame-retardant treatment of textile materials, including cellulosic (e.g. cotton) materials, consists of impregnation of the material with an aqueous solution of a treatment agent which is a poly(hydroxyorgano)phosphonium compound. This compound may be a salt, for example a tetrakis(hydroxyorgano)phosphonium salt. Alternatively, the compound may be a condensate, for example a condensate of a tetrakis(hydroxyorgano)phosphonium salt with a nitrogen-containing compound such as urea. Following impregnation, the material is dried and then cured with ammonia to produce a cured, water-insoluble polymer which is mechanically fixed within the fibres of the material. After curing, the polymer is oxidised to convert trivalent phosphorus to pentavalent phosphorus and the material is washed and dried.

Such a process is described in, for example, GB2205868, GB 2290562 and GB2294479.

In the curing process ammonia gas may be passed directly into a chamber through which the material passes, or, preferably, ammonia gas is forced through the material inside the chamber. GB1439608 and GB1439609 describe apparatus for use in such a process, which consists of a closed chamber, entry and exit seals thereto through which the material moves, a duct located in the chamber and having one or more orifices through which gaseous ammonia issues and subsequently passes through the material passing over each orifice, the chamber having means to prevent condensed water from dripping on to the material. This type of unit will hereinafter be described as a standard cure unit.

A high speed cure unit is described in GB2252570, where the ammonia feed rate is precisely controlled relative to the amount of material being processed and the curing chamber is pre-filled with ammonia to provide a reservoir of ammonia to allow for any slight variation in the ammonia usage relative to the ammonia input. This type of unit will hereinafter be described as a high speed cure unit.

However, it has been identified that known methods of treating materials with poly(hydroxyorgano)phosphonium compound result in effluent that has significant levels of water soluble phosphorus species present. Water soluble phosphorus species may be considered a hazard. Therefore environmental standards in many countries place limits on the amount of such phosphorus that can be included in waste before it is released to the environment.

This means that when carrying out such methods it is necessary to treat the effluent to remove water soluble phosphorous species, which increases cost and complexity.

Where reference is made to "water soluble phosphorus species" this means species that have a solubility of at least 10 g/l at 25° C.

In particular, the effluent commonly has THPO as the majority water soluble phosphorus species. The removal of this THP salt tends to involve prolonged and harsh oxidation treatments—for example oxidation with hydrogen peroxide under acid conditions or oxidation with hydrogen peroxide under UV.

Therefore there is a need for a technique which enables effluent to be produced that has water soluble phosphorus species present in the form of species that are more readily removed/can be removed without harsh treatment.

SUMMARY OF THE INVENTION

The present invention provides, in a first aspect, a method for treating textile material to confer flame retardant properties, the method comprising the steps of:
  (a) impregnating the material with an aqueous solution of a treatment agent which is a poly(hydroxyorgano)phosphonium compound;
  (b) drying the impregnated material;
  (c) curing the dried impregnated material with ammonia to produce a cured, water-insoluble polymer which is mechanically fixed within the fibres of the material;
  (d) oxidising the cured polymer to convert trivalent phosphorus to pentavalent phosphorus;
  (e) washing and drying the material;
wherein one or both of steps (d) and (e) result in the co-production of an aqueous effluent;
wherein the conditions are controlled such that the atomic ratio of N:P present on the material increases during step (c) by 0.8 or more.

The present invention also provides, in a second aspect, the use of an increase in atomic ratio of N:P during curing of 0.8 or more to reduce the amount of phosphorus present in the effluent produced in a flame retardant treatment for textile materials.

The present invention also provides, in a third aspect, the use of an increase in atomic ratio of N:P during curing of 0.8 or more to increase the amount of phosphorus present in the form of 1,3,5-triaza-7-phosphaadamantane and derivatives thereof, in the effluent produced in a flame retardant treatment for textile materials.

In the second and third aspects, the flame retardant treatments may be any processes for the flame-retardant treatment of textile materials, including cellulosic (e.g. cotton) materials, such as those which consist of impregnation of the material with an aqueous solution of a treatment agent which is a poly(hydroxyorgano)phosphonium compound, followed by drying and curing with ammonia to produce a cured, water-insoluble polymer which is mechanically fixed within the fibres of the material, with subsequent oxidisation of the polymer to convert trivalent phosphorus to pentavalent phosphorus.

In one embodiment, the flame retardant treatments may be methods comprising steps (a) to (e) as defined in the first aspect.

The invention provides, in a fourth aspect, a method of producing 1,3,5-triaza-7-phosphaadamantane and/or derivatives thereof, the method comprising the steps of:
  (a) impregnating the material with an aqueous solution of a treatment agent which is a poly(hydroxyorgano)phosphonium compound;
  (b) drying the impregnated material;

(c) curing the dried impregnated material with ammonia to produce a cured, water-insoluble polymer which is mechanically fixed within the fibres of the material;
(d) oxidising the cured polymer to convert trivalent phosphorus to pentavalent phosphorus;
(e) washing and drying the material;
wherein one or both of steps (d) and (e) result in the co-production of an aqueous effluent;
wherein the conditions are controlled such that the atomic ratio of N:P present on the material increases during step (c) by 0.8 or more, so that the aqueous effluent contains 1,3,5-triaza-7-phosphaadamantane and/or derivatives thereof.

DETAILED DESCRIPTION OF PREFERRED EMBODIMENTS

Surprisingly, when carrying out the method of the present invention, the phosphorus in the effluent is mainly in the form of 1,3,5-triaza-7-phosphaadamantane (PTA) and/or derivatives thereof. In particular, 1,3,5-triaza-7-phosphaadamantane (PTA) may be present, and/or 1,3,5-triaza-7-phosphaadamantane oxide (PTAO) may be present, and/or the N-methyl form of PTAO (Me-PTAO) may be present and/or the N-oxide form of PTAO may be present.

The exact form of the derivatives of 1,3,5-triaza-7-phosphaadamantane (PTA) present will depend upon the conditions used. For example, the N-methyl form of PTAO is believed to be formed in the presence of high amounts of formaldehyde during or after the cure stage.

It is possible that derivatives of PTA other than 1,3,5-triaza-7-phosphaadamantane oxide (PTAO), the N-methyl form of PTAO (Me-PTAO) and the N-oxide form of PTAO may be present.

In one embodiment, 50 wt % or more, such as 55 wt % or more, 60 wt % or more, 70 wt % or more, 80 wt % or more, or 90 wt % or more, of the water soluble phosphorus species in the effluent may be present in the form of 1,3,5-triaza-7-phosphaadamantane and/or derivatives thereof (hereinafter referred to as "PTA species").

In particular, it has surprisingly been found that as much as 70 to 80 wt % or more, such as 80 to 90 wt % or more, of the water soluble phosphorus species in the effluent may be present in the form of PTA species when the method of the invention is carried out. This is advantageous as such PTA species, being amines, can be more readily removed from the effluent and in particular do not require harsh removal conditions. For example, ion exchange techniques may be used to readily remove such species.

The PTA species may in particular be one or more species selected from:
1,3,5-triaza-7-phosphaadamantane (PTA),
1,3,5-triaza-7-phosphaadamantane oxide (PTAO),
the N-methyl form of PTAO (Me-PTAO), and
the N-oxide form of PTAO.

The skilled man will be aware of methods for determining N and P levels, and hence an N:P ratio, for both before and after the curing step (c). For example, gravimetric analysis and colorimetric analysis may be mentioned for measuring P levels and Kjeldahl analysis and colorimetric analysis may be mentioned for measuring N levels.

In a preferred embodiment, the method of the first or fourth aspect of the invention further comprises a step of:
removing 1,3,5-triaza-7-phosphaadamantane and/or derivatives thereof from the aqueous effluent.

The aqueous effluent may be from step (d) or from step (e) or from both step (d) and step (e). In a preferred embodiment, aqueous effluent from step (d) and step (e) is combined and then 1,3,5-triaza-7-phosphaadamantane and/or derivatives thereof are removed from the combined effluent.

Some or all of the 1,3,5-triaza-7-phosphaadamantane and/or derivatives thereof present in the effluent may be removed from the aqueous effluent. In one embodiment, 25 wt % or more of the PTA species present in the effluent are removed, such as 50 wt % or more, preferably 70 wt % or more, such as 75 wt % or more, 80 wt % or more, 90 wt % or more, 95 wt % or more, or 99 wt % or more.

In one embodiment, the PTA species are removed using ion exchange. This may suitably be strong acid cation exchange resin, such as sulphuric acid cation exchange resin. Any suitable flow rate may be used. When expressed in bed volume/hour (BV/hr) a flow rate of, for example, from 8 to 100 BV/hour may be used, such as a flow rate of about 20 to 40 BV/hr.

In another embodiment PTA species which are phosphines may be removed using organic solvents, such as chloroform and ethanol, following concentration of the effluent by evaporation.

In another embodiment a reactive filtration system may be used. This may in particular be used for PTA species which are phosphine oxides. In such a system a coating is used on the filter media (e.g. sand) that is used in the filtration system, with the coating having been selected as one which will adsorb the PTA species in question. For example, a ferric coating such as a hydrous ferric oxide coating may be selected.

Other filtration methods such as coagulation filtration may also be considered.

The PTA species may be removed at any stage after step (c).

In the method of the first aspect, the PTA species may, for example, be removed after step (c) and before step (d), or, preferably, may be removed after step (d). In the latter case, the PTA species may be removed before, during or after step (e).

In one embodiment the PTA species are removed after step (e).

The PTA species may be isolated after they have been removed.

In one embodiment, the conditions are controlled so that the atomic ratio of N:P present on the material increases during step (c) by 0.9 or more, preferably 1.0 or more, more preferably by 1.1 or more, such as by 1.2 or more; most preferably by 1.3 or more. In a preferred embodiment the increase is by 1.4 or more, e.g. by 1.5 or more.

It may be that the conditions are controlled so that the atomic ratio of N:P present on the material increases during step (c) by at least 0.8 and up to 2.0, such as by at least 0.9 and up to 1.9, e.g. by at least 1.0 and up to 1.8, for example by at least 1.2 and up to 1.7.

In one preferred embodiment the conditions are controlled so that the atomic ratio of N:P present on the material increases during step (c) by at least 1.2 and up to 2.0, such as by at least 1.3 and up to 1.9, e.g. by at least 1.4 and up to 1.8.

It will be appreciated by the skilled man that the N:P ratio in the material would decrease somewhat during the oxidation and washing steps (d) and (e). The references to the N:P ratio after curing therefore refer to the ratio measured after step (c) is carried out, but before step (d) oxidation occurs. In particular, the ratio may be measured immediately before step (d) oxidation.

Preferably, the conditions are controlled so that the atomic ratio of N:P present on the material after the curing step (c) is 2.3 or higher, such as 2.4 or higher, e.g. 2.5 or higher, such as 2.6 or higher. In one embodiment, that the atomic ratio of N:P present on the material after the curing step (c) is from 2.3 to 3.5, such as from 2.4 to 3.0.

The conditions that may be controlled are suitably:
(i) the cure unit selected for curing in step (c);
(ii) the speed of travel of the fabric selected during curing in step (c);
(iii) the amount of ammonia used for curing in step (c).

As the skilled man would appreciate, these conditions may be selected bearing in mind the type of material to be treated. However, for a given material the conditions may be controlled as follows to achieve a greater increase in N:P ratio during ammonia curing:

(i) The Cure Unit Selected for Curing in Step (c).

In step (c) a standard cure unit or a high speed cure unit may be used. The use of a high speed cure unit will increase the N:P ratio.

(ii) The Speed of Travel of The Fabric Selected During Curing in Step (c)

The cure chamber usually contains 1 to 20 m of fabric. A standard cure unit may usually contain about 1 m of fabric, whilst a high speed cure unit may usually contain about 15 m of fabric.

The use of a lower speed of travel will increase the N:P ratio.

For a standard cure unit the speed of travel may be selected to be from 5 to 15 m/min. Preferably, the speed of travel is selected to be from 5 to 10 m/min, e.g. from 5 to 8 m/min.

For a high speed cure unit the speed of travel may be selected to be from 15 to 60 m/min. Preferably, the speed of travel is selected to be from 15 to 40 m/min, e.g. from 15 to 25 m/min.

(iii) The Amount of Ammonia Used for Curing in Step (c)

In order to increase the N:P ratio during curing step (c) the molar relationship between the ammonia input and the phosphorus in the treatment agent on the fabric is preferably selected to be 3.2:1 or higher in a standard cure unit and to be 1.9:1 or higher in a high speed cure unit.

For a standard cure unit the molar relationship between the ammonia input and the phosphorus in the treatment agent on the fabric is preferably selected to be 3.3:1 or higher, such as 3.4 or higher.

For a high speed cure unit the molar relationship between the ammonia input and the phosphorus in the treatment agent on the fabric is preferably selected to be 2.0:1 or higher, such as 2.1:1 or higher.

Preferred Conditions

It is therefore the case that preferably the cure unit is selected to be a standard cure unit or a high speed cure unit and then one or both of:
the speed of travel for the fabric during curing in step (c), and
the molar relationship between the ammonia input and the phosphorus in the treatment agent on the fabric,
are selected in view of the type of unit used.

In one embodiment, the conditions controlled are:
1. selecting whether a standard cure unit or a high speed cure unit is used in step (c);
and then:
2. selecting a low speed of travel for the fabric during curing in step (c), such that for a standard cure unit the speed of travel is from 5 to 15 m/min and for a high speed cure unit the speed of travel is from 15 to 60 m/min; and
3. selecting the molar relationship between the ammonia input and the phosphorus in the treatment agent on the fabric, such that for a standard cure unit it is 3.2:1 or and for a high speed cure unit it is 1.9:1 or higher.

In a preferred embodiment, the conditions controlled are
1. selecting whether a standard cure unit or a high speed cure unit is used in step (c);
and then:
2. selecting a low speed of travel for the fabric during curing in step (c), such that for a standard cure unit the speed of travel is from 5 to 10 m/min and for a high speed cure unit the speed of travel is from 15 to 40 m/min; and
3. selecting the molar relationship between the ammonia input and the phosphorus in the treatment agent on the fabric, such that for a standard cure unit it is 3.3:1 or and for a high speed cure unit it is 2.0:1 or higher.

Other preferred/optional features of the methods/uses of the invention will be discussed below.

(A) The Poly(Hydroxyorgano) Phosphonium Compound Used.

The poly(hydroxyorgano)phosphonium compound may suitably be a tetra(hydroxyorgano)phosphonium compound.

In the poly(hydroxyorgano)phosphonium compound, each hydroxyorgano group is preferably an alpha hydroxyorgano group of 1-9 carbons, especially one of formula:

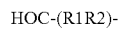

HOC-(R1R2)- wherein each of R1 and R2, which may be the same or different, represents hydrogen or an alkyl group of 1 to 4 carbons e.g. methyl or ethyl. Preferably R1 is hydrogen and in one embodiment both R1 and R2 are hydrogen, as in tetrakis (hydroxymethyl)phosphonium (THP) compounds.

The poly(hydroxyorgano)phosphonium compound may in one preferred embodiment be a tetrakis(hydroxyalkyl)phosphonium salt.

Alternatively, in another preferred embodiment the poly (hydroxyorgano)phosphonium compound may be a condensate of a tetrakis(hydroxyalkyl)phosphonium salt with a nitrogen-containing compound.

Preferably, the method uses a THP salt or a THP condensate.

In principal, any water soluble THP salt with an anion which does not interact adversely with other components present may be used. Preferably, a tetrakis(hydroxymethyl) phosphonium salt of formula THPX, wherein X is chloride, sulphate, bromide, iodide, phosphate, acetate, oxalate, citrate, borate, chlorate, lactate, nitrate, fluoride, carbonate or formate is used.

THP condensates are water soluble or sparingly water soluble copolymers of THP with organic nitrogen compounds, such as urea or an amine. In one embodiment, the condensate is a copolymer of THP with urea, a C1-C20 alkylamine, dicyandiamide, thiourea or guanidine. The molar ratio of THP to nitrogen compound may be, for example, 2:1 or higher, such as 3:1 or higher, preferably 4:1 or higher, such as 5:1 or higher, for instance from 5:1 to 7:1 molar THP: nitrogen compound.

THP condensates may contain two or more phosphorus atoms, so long as the phosphorus compound is water soluble to a concentration of at least 0.5 g/l at 25° C. Such phosphorus compounds contain a total of at least two hydroxymethyl groups, usually at least one per phosphorus atom, and preferably at least two hydroxymethyl groups per phosphorus atom. In the THP condensate the group or groups joining the phosphorus atoms together may be of the formula —R—, —R—O—, —R—O—R—, —R—NH—R or —R—R"—R where R is an alkylene group of 1 to 4 carbon atoms and R" is the residue formed by removal of two hydrogen atoms, bonded to nitrogen, from a di or polyamide or an amine or di or polyamine, such as urea, a C1-C20 alkylamine, dicyandiamide, thiourea or guanidine. Such compounds with two or more, e.g. three, hydroxyalkyl groups per phosphorus atom may be made by self condensation of THP salts with a compound of general formula R"H$_2$ such as urea, or a C1-C20 alkylamine, e.g. by heating at 40 to 120° C.

(B) The Amount of Poly(Hydroxyorgano) Phosphonium Compound Used.

The skilled man would readily be able to select appropriate amounts of poly(hydroxyorgano)phosphonium compound based on the fabric to be treated (in particular the fabric density) and its intended end use (in particular the standard and durability criteria the treated fabric will need to meet).

The amount of poly(hydroxyorgano)phosphonium compound used in the aqueous impregnating solution in step (a) will usually be calculated so as to give a 30 to 50% add on. This will require an appropriate concentration of poly(hydroxyorgano)phosphonium compound in the treatment solution to be selected, based on the pick up rate. For example, a 40% add on would be achieved by use of a 50% solution with an 80% pick up rate.

The amount of poly(hydroxyorgano)phosphonium compound used in the aqueous impregnating solution in step (a) may, for example, be from 5 to 50% (expressed by weight as THP+ ion). If desired, the solution may contain a wetting agent, e.g. a nonionic or cationic wetting agent.

(C) The Moisture Content of the Fabric Prior to Curing Step (c).

In step (b) the material may be dried to any suitable level, such as from 0 to 20%, the percentage being calculated from the increase in weight of the fabric and the weight of chemicals impregnated.

In one embodiment the material is dried to a residual moisture content of from 3 to 15%, such as from 4 to 8%.

These values are actual moisture content values rather than values as obtained from a conductivity meter. As the skilled man would understand, moisture values taken using a conductivity meter have to be adjusted to take into account the contribution from ions present.

The drying may be in a stenter oven or over heated cans e.g. steam cans. It may involve heating, e.g. at from 80 to 120° C., for a suitable period of time, such as from 1 minute to 10 minutes.

(D) The Batching Time Used After Step (c) and Before Step (d).

The material may be batched for any suitable period of time, such as one hour or more, prior to oxidation.

In a standard cure unit a batching time of from 30 minutes to 8 hours may suitably be used, such as from 1 to 8 hours.

In a high speed cure unit a batching time of from 0 to 8 hours may suitably be used, such as from 1 to 8 hours.

(E) Textile Material

The textile material may comprise substantially 100% cellulosic fibres (e.g. cotton, linen, jute, hessian or regenerated cellulosic material).

Alternatively, the textile material may comprise both cellulosic fibres, and non-cellulosic fibres. The non-cellulosic fibres may be, for example, wool or silk fibres or they may comprise synthetic fibres such as polyester, polyamide, acrylic or aramid fibres.

In one embodiment, the textile material is substantially made from cellulosic (e.g. cotton) fibres.

In another embodiment, the textile material is made from cotton fibres and polyester fibres, for example 60% cotton fibres and 40% polyester fibres.

The textile material is preferably one with a weight of from 50 to 1000 g/m$^2$, e.g. from 150 to 400 g/m$^2$.

(F) Other Curing Conditions

In step (c) the ammonia gas may be passed directly into a chamber through which the material passes, or the ammonia gas may be injected through the material inside the chamber.

Typically a standard cure unit may be operated at a temperature of from 50 to 60° C., whilst a high speed cure unit may be operated at a temperature of from 45 to 80° C. Generally a higher temperature, such as from 60 to 80° C., may lead to an increase in the N:P ratio. However, in practice there tends to be little scope to closely control the temperature of the curing step.

The fresh ammonia gas is preferably undiluted, but may be diluted with up to 30% by volume of steam or air. The ammonia gas issuing from the duct into the chamber may be at from 10 to 120° C. but is preferably at a temperature below 100° C., e.g. from 40° C. to 50° C.

The invention will now be further illustrated, in a non-limiting manner, by the following Examples.

EXAMPLES

Preparation Example A

Preparation of Fabric to be Cured

A precondensate of tetrakis(hydroxymethyl)phosphonium chloride (THPC) and urea was prepared; the precondensate was diluted with water to give a solution with the equivalent of 25% THP+ ion.

1000 metres of vat-dyed 160 cm wide cotton drill weighing 280 g/m$^2$ was padded through this solution to give approximately 80% wet pick up. The fabric was then dried using a stenter dryer machine in tandem with the padding mangle. The stenter was set to a temperature of approximately 100° C. and the speed adjusted to give an actual fabric moisture content of 4 to 8%.

Example 1

Standard Cure Unit

Curing Conditions

Fabric prepared in accordance with preparation example A was cured in a standard cure unit at a speed of 12 m/min and using an ammonia input rate of 3.3:1 ammonia to phosphorus.

Oxidation Conditions

The cured fabric was jig oxidised using a dilute hydrogen peroxide solution.

Testing

Fabric samples were taken before and after curing. The N and P levels in the samples were measured for determination of nitrogen to phosphorus ratio (N:P) increase.

The resultant aqueous effluent from the hydrogen peroxide treatment stage was analysed by P31 NMR, to determine the % of the water soluble P species present that was made up of PTA species.

Results

Fabric N:P increase after curing=1.5

Level of PTA species observed in P31 NMR=80%

Example 2

Standard Cure Unit

Curing Conditions

Fabric prepared in accordance with preparation example A was cured in a standard cure unit at a speed of 20 m/min and using an ammonia input rate of 3.3:1 ammonia to phosphorus.

Oxidation Conditions

The cured fabric was jig oxidised using a dilute hydrogen peroxide solution.

Testing

Fabric samples were taken before and after curing. The N and P levels in the samples were measured for determination of nitrogen to phosphorus ratio (N:P) increase.

The resultant aqueous effluent from the hydrogen peroxide treatment stage was analysed by P31 NMR, to determine the % of the water soluble P species present that was made up of PTA species.

Results

Typical fabric N:P increase after curing=1.1
Typical level of PTA species observed in P31 NMR=30%

Conclusion

It can be seen that increasing the speed as compared to Example 1 leads to a lower N:P increase, and a lower amount of PTA species.

Example 3

High Speed Cure Unit

Curing Conditions

Fabric prepared in accordance with preparation example A was cured in a high speed cure unit at a speed of 40 m/min and using an ammonia input rate of 2:1 ammonia to phosphorus.

Oxidation Conditions

The cured fabric was jig oxidised using a dilute hydrogen peroxide solution.

Testing

Fabric samples were taken before and after curing. The N and P levels in the samples were measured for determination of nitrogen to phosphorus ratio (N:P) increase.

The resultant aqueous effluent from the hydrogen peroxide treatment stage was analysed by P31 NMR, to determine the % of the water soluble P species present that was made up of PTA species.

Results

Typical fabric N:P increase after curing=1.6
Typical level of PTA species observed in P31 NMR=80%

Example 4

High Speed Cure Unit

Curing Conditions

Fabric prepared in accordance with preparation example A was cured in a high speed cure unit at a speed of 40 m/min and using an ammonia input rate of 1:1 ammonia to phosphorus.

Oxidation Conditions

The cured fabric was jig oxidised using a dilute hydrogen peroxide solution.

Testing

Fabric samples were taken before and after curing. The N and P levels in the samples were measured for determination of nitrogen to phosphorus ratio (N:P) increase.

The resultant aqueous effluent from the hydrogen peroxide treatment stage was analysed by P31 NMR, to determine the % of the water soluble P species present that was made up of PTA species.

Results

Fabric N:P increase after curing=1.0
Level of PTA species observed in P31 NMR=14%

Conclusion

It can be seen that reducing the ammonia input ratio, as compared to Example 3, leads to a lower N:P increase, and a lower amount of PTA species.

Example 5

Laboratory Scale High Speed Cure Unit

Treatment Conditions

A precondensate of tetrakis(hydroxymethyl)phosphonium chloride (THPC) and urea was prepared; the precondensate was diluted with water to give a solution with the equivalent of 25% THP+ ion.

10 meters of vat-dyed 45 cm wide cotton drill weighing 280 g/m$^2$ was padded through this solution to give approximately 80% wet pick up. The fabric was then dried using a Laboratory BENZ dryer machine in tandem with the padding mangle. The BENZ was set to a temperature of approximately 100° C. and drying time of 1 minute. After drying the fabric was allowed to re-condition in air to a moisture content of 4 to 8%.

The fabric was then cured in a laboratory scale high speed cure unit at a speed of 5 m/min using an ammonia input rate of 2:1 ammonia to phosphorus.

Testing

Fabric samples were taken before and after curing. The N and P levels in the samples were measured for determination of nitrogen to phosphorus ratio (N:P) increase.

One of the samples taken after curing was washed with water and the water extract analysed by P31 NMR to determine the % of the water soluble P species present that was made up of PTA species.

The resultant aqueous effluent from the hydrogen peroxide treatment stage was also analysed by P31 NMR, to determine the % of the water soluble P species present that was made up of PTA species.

Results

Fabric N:P increase after curing=1.6
Level of PTA species observed in P31 NMR for water extract after curing=80%
Level of PTA species observed in P31NMR for effluent from jig oxidation=80%.

Example 6

Removal of PTA Species

The effluent from Example 1 was treated to remove the PTA species present.

Method 2 liters of effluent was passed through a column containing 100 ml of strong acid cation exchange resin, using a flow rate of 3 liters/hr (30 BV/hr).

P31 NMR was used to analyse the subsequent effluent from the column.

The resin was regenerated with 10% sulphuric acid and the PTA species were eluted.

Result

P31 NMR of the effluent from the column showed that 100% of the PTA species present in the effluent from Example 1 was removed from the effluent by the column treatment.

The invention claimed is:

1. A method for conferring flame retardant properties to a textile material, comprising the steps of:
    (a) impregnating the material with an aqueous solution of a treatment agent comprising a poly(hydroxyorgano) phosphonium compound;

(b) drying the impregnated material;
(c) curing the dried impregnated material with ammonia to produce a cured water-insoluble polymer, wherein:
said polymer is mechanically fixed within the fibers of the material, and
said curing increases the atomic ratio of N:P by at least 0.8;
(d) oxidizing the cured polymer to convert trivalent phosphorus to pentavalent phosphorus; and
(e) washing and drying the material;
wherein one or both of steps (d) and (e) result in the co-production of an aqueous effluent which comprises 1,3,5-triaza-7-phosphaadamantane and/or derivatives thereof and said method further comprises removing said 1,3,5-triaza-7-phosphaadamantane and/or derivatives thereof from said aqueous effluent.

2. The method of claim 1, wherein the 1,3,5-triaza-7-phosphaadamantane derivatives comprise 1,3,5-triaza-7-phosphaadamantane oxide.

3. The method of claim 2, wherein said 1,3,5-triaza-7-phosphaadamantane oxide comprises an N-methyl form of 1,3,5-triaza-7-phosphaadamantane oxide, an N-oxide form of 1,3,5-triaza-7-phosphaadamantane oxide, or a combination thereof.

4. The method of claim 1, wherein at least 70 wt % of the 1,3,5-triaza-7-phosphaadamantane and/or its derivatives is removed.

5. The method of claim 4, wherein at least 90 wt % of the 1,3,5-triaza-7-phosphaadamantane and/or its derivatives is removed.

6. The method of claim 1, wherein the 1,3,5-triaza-7-phosphaadamantane and/or its derivatives are removed by ion exchange.

7. The method of claim 1, further comprising isolating the 1,3,5-triaza-7-phosphaadamantane and/or its derivatives after removal from said effluent.

8. The method of claim 1 wherein the atomic ratio of N:P is increased by at least 1.0.

9. The method of claim 1 wherein the atomic ratio of N:P is increased in an amount of from 1.4 to 2.0.

10. The method of claim 1, wherein the atomic ratio of N:P is increased in the curing step by control of conditions comprising:
(i) choice of cure unit,
(ii) speed of travel of the textile material during curing in step (c), and
(iii) the molar ratio of ammonia added to phosphorus in the treatment agent during the curing step.

11. The method of claim 10, wherein:
(i) the cure unit comprises a standard cure unit;
(ii) the speed of the travel of the textile material during curing in step (c) ranges from 5 to 15 m/min, and
(iii) the molar ratio of added ammonia to phosphorus in the treatment agent is 3.2:1 or higher.

12. The method of claim 10, wherein:
(i) the cure unit comprises a high speed cure unit;
(ii) the speed of the travel of the textile material during curing in step (c) ranges from 15 to 60 m/min, and
(iii) the molar ratio of added ammonia to phosphorus in the treatment agent is 1.9:1 or greater.

13. The method of claim 11, wherein:
(i) the speed of the travel of the textile material during curing in step (c) ranges from 5 to 10 m/min, and
(ii) the molar ratio of added ammonia to phosphorus in the treatment agent is 3.3:1.

14. The method of claim 12, wherein:
(i) the speed of the travel of the textile material during curing in step (c) ranges from 15 to 40 m/min, and
(ii) the molar ratio of added ammonia to phosphorus in the treatment agent is 2.0:1 or greater.

* * * * *

UNITED STATES PATENT AND TRADEMARK OFFICE
CERTIFICATE OF CORRECTION

PATENT NO. : 8,580,348 B2  Page 1 of 1
APPLICATION NO. : 13/132561
DATED : November 12, 2013
INVENTOR(S) : Hand et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 200 days.

Signed and Sealed this
Twenty-second Day of September, 2015

Michelle K. Lee
*Director of the United States Patent and Trademark Office*